(12) United States Patent
Shimada et al.

(10) Patent No.: US 12,128,074 B2
(45) Date of Patent: Oct. 29, 2024

(54) EXTERNAL AGENT FOR HAIR GROWTH OR HAIR LOSS PREVENTION

(71) Applicant: NICHINICHI PHARMACEUTICAL CO., LTD., Iga (JP)

(72) Inventors: Takashi Shimada, Iga (JP); Mamoru Kitamura, Iga (JP)

(73) Assignee: NICHINICHI PHARMACEUTICAL CO., LTD., Iga (JP)

(*) Notice: Subject to any disclaimer, the term of this patent is extended or adjusted under 35 U.S.C. 154(b) by 778 days.

(21) Appl. No.: 17/291,341

(22) PCT Filed: Nov. 8, 2019

(86) PCT No.: PCT/JP2019/044000
§ 371 (c)(1),
(2) Date: May 5, 2021

(87) PCT Pub. No.: WO2020/096059
PCT Pub. Date: May 14, 2020

(65) Prior Publication Data
US 2021/0393708 A1 Dec. 23, 2021

(30) Foreign Application Priority Data
Nov. 9, 2018 (JP) .................. 2018-211211

(51) Int. Cl.
*A61K 35/744* (2015.01)
*A61K 8/99* (2017.01)
*A61P 17/14* (2006.01)
*A61Q 5/06* (2006.01)

(52) U.S. Cl.
CPC .............. *A61K 35/744* (2013.01); *A61K 8/99* (2013.01); *A61P 17/14* (2018.01); *A61Q 5/06* (2013.01)

(58) Field of Classification Search
None
See application file for complete search history.

(56) References Cited

U.S. PATENT DOCUMENTS

| | | | |
|---|---|---|---|
| 2018/0256490 A1 | 9/2018 | Kim et al. | |
| 2019/0183943 A1* | 6/2019 | Yum | A61K 9/0053 |

FOREIGN PATENT DOCUMENTS

| | | |
|---|---|---|
| JP | H05-201871 A | 8/1993 |
| JP | H08-99887 A | 4/1996 |
| JP | H08-259450 A | 10/1996 |
| JP | H08-283166 A | 10/1996 |
| JP | H08-295631 A | 11/1996 |
| JP | 109-048733 A | 2/1997 |

(Continued)

OTHER PUBLICATIONS

Choi, Eun-Ju; et al; "Effect of Enterococcus faecalis EF-2001 on experimentally induced atopic eczema in mice" Food Science Biotechnology, 25, 1087-1093, 2016 (Year: 2016).*

(Continued)

*Primary Examiner* — David W Berke-Schlessel
(74) *Attorney, Agent, or Firm* — MH2 Technology Law Group, LLP

(57) ABSTRACT

The present invention relates to an external agent for growing hair or preventing hair loss comprising at least one member selected from the group consisting of cells of lactic acid bacteria belonging to the genus *Enterococcus* and cell components thereof.

4 Claims, 3 Drawing Sheets

(56) References Cited

FOREIGN PATENT DOCUMENTS

| | | |
|---|---|---|
| JP | 2004-210659 A | 7/2004 |
| JP | 2016-84303 A | 5/2016 |
| JP | 2017-001961 A | 1/2017 |
| JP | 2018-529720 A | 10/2018 |
| KR | 10-2009-0051586 A | 5/2009 |
| KR | 10-1840376 B1 | 3/2018 |
| KR | 10-2019-0041865 A | 4/2019 |
| KR | 10-2019-00418654 A | 4/2019 |
| WO | WO-2018135843 A2 * | 7/2018 ........... A23L 33/135 |

OTHER PUBLICATIONS

International Search Report (with English translation) mailed Dec. 24, 2019 for corresponding International Application No. PCT/JP2019/044000, 4 pages.

* cited by examiner

EXTERNAL AGENT FOR HAIR GROWTH OR HAIR LOSS PREVENTION

CROSS-REFERENCE TO RELATED APPLICATIONS

This application is a U.S. National Stage application of PCT/JP2019/044000, filed 8 Nov. 2019, which claims priority to Japanese Application No. 2018-211211, filed 9 Nov. 2018, the entire disclosures of which are incorporated herein by reference in their entireties.

TECHNICAL FIELD

The present invention relates to an external agent for growing hair and preventing hair loss.

BACKGROUND ART

Lactic acid bacteria belonging to the genus *Enterococcus* are known to have various effects on living organisms.

For example, an *Enterococcus faecalis* NF-1011 strain has been reported to have the following effects: inhibition of blood pressure increase and prevention of cardiac hypertrophy (Patent Literature 1), immunostimulation effects (Patent Literature 2), enhancement of interferon production (Patent Literature 3), protection against infection (Patent Literature 4), enhancement of anti-cancer (Patent Literature 5), reduction of anti-cancer drug toxicity (Patent Literature 6), and activation of biological antioxidant capacity (Patent Literature 7).

However, Patent Literature 1 to 7 basically disclose oral administration of lactic acid bacteria, and do not assume their use as external agents.

CITATION LIST

Patent Literature

PTL 1: JP1993-201871A
PTL 2: JP1996-99887A
PTL 3: JP1996-259450A
PTL 4: JP1996-283166A
PTL 5: JP1996-295631A
PTL 6: JP1997-48733A
PTL 7: JP2017-1961A

SUMMARY OF INVENTION

Technical Problem

The present invention aims to provide an external agent with excellent effects of growing hair and preventing hair loss.

Solution to Problem

To achieve the above object, the present inventors conducted extensive research. As a result, they found that the cells of an *Enterococcus faecalis* NF-1011 strain and cell components thereof exhibit significantly high effects of hair growth and hair loss prevention.

The present invention was accomplished as a result of further research based on the above findings. The present invention provides the following external agent for growing hair or preventing hair loss.

Item 1. An external agent for growing hair or preventing hair loss comprising at least one member selected from the group consisting of cells of lactic acid bacteria belonging to the genus *Enterococcus* and cell components thereof.

Item 2. The external agent according to Item 1, wherein the lactic acid bacteria belonging to the genus *Enterococcus* are *Enterococcus faecalis*.

Item 3. The external agent according to Item 1 or 2, wherein the lactic acid bacteria belonging to the genus *Enterococcus* are *Enterococcus faecalis* NF-1011 strain (FERN BP-10902).

Item 4. The external agent according to any one of Items 1 to 3, wherein the cells are dead cells.

Item 5. The external agent according to any one of Items 1 to 4, wherein the cell component of lactic acid bacteria is a component obtained by subjecting the lactic acid bacteria to a lytic enzyme treatment and a heat treatment.

Item 6. A method for growing hair or preventing hair loss, comprising the step of applying at least one member selected from the group consisting of cells of lactic acid bacteria belonging to the genus *Enterococcus* and cell components thereof to the skin of a mammal in need for growing hair or preventing hair loss.

Item 7. The method according to Item 6, wherein the lactic acid bacteria belonging to the genus *Enterococcus* are *Enterococcus faecalis*.

Item 8. The method according to Item 6 or 7, wherein the lactic acid bacteria belonging to the genus *Enterococcus* are *Enterococcus faecalis* NF-1011 strain (FERM BP-10902).

Item 9. The method according to any one of Items 6 to 8, wherein the cells are dead cells.

Item 10. The method according to any one of Items 6 to 9, wherein the cell component of lactic acid bacteria is a component obtained by subjecting the lactic acid bacteria to a lytic enzyme treatment and a heat treatment.

Item 11. Use of at least one member selected from the group consisting of cells of lactic acid bacteria belonging to the genus *Enterococcus* and cell components thereof in the production of an external agent for growing hair or preventing hair loss.

Item 12. The use according to Item 11, wherein the lactic acid bacteria belonging to the genus *Enterococcus* are *Enterococcus faecalis*.

Item 13. The use according to Item 11 or 12, wherein the lactic acid bacteria belonging to the genus *Enterococcus* are *Enterococcus faecalis* NF-1011 strain (FERN BP-10902).

Item 14. The use according to any one of Items 11 to 13, wherein the cells are dead cells.

Item 15. The use according to any one of Items 11 to 14, wherein the cell component of lactic acid bacteria is a component obtained by subjecting the lactic acid bacteria to a lytic enzyme treatment and a heat treatment.

Advantageous Effects of Invention

Since cells of lactic acid bacteria belonging to the genus *Enterococcus* and cell components thereof have significantly high effects of hair growth and hair loss prevention, they are useful as active ingredients of an external agent for growing hair or preventing hair loss.

DESCRIPTION OF EMBODIMENTS

Figure 1:
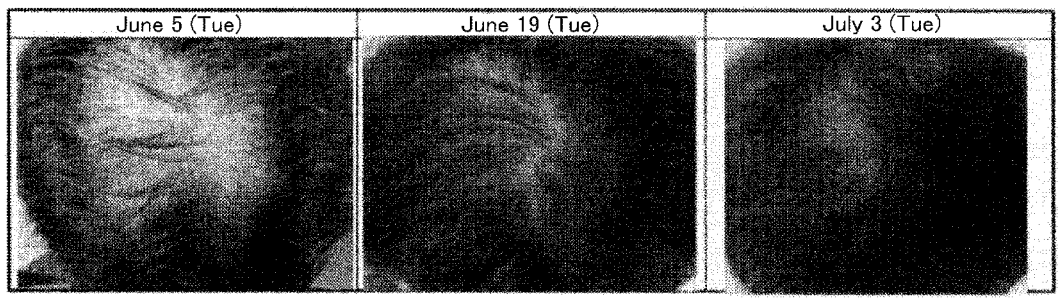
FIG. 1 shows photographs representing the crown of the head of a male subject in Test Example 1.

The embodiments of the present invention are detailed below.

In the present specification, the term "comprise" includes the meanings of essentially consisting of and consisting of.

The external agent for growing hair or preventing hair loss according to the present invention comprises at least one member selected from the group consisting of cells of lactic acid bacteria belonging to the genus *Enterococcus* and cell components thereof.

The lactic acid bacteria belonging to the genus *Enterococcus* are not particularly limited. Examples include *Enterococcus faecalis, Enterococcus faecium, Enterococcus avium, Enterococcus casseliflavus, Enterococcus gallinarum, Enterococcus flavescens*, and the like. Of these, *Enterococcus faecalis, Enterococcus faecium*, or the like are preferred, and *Enterococcus faecalis* is more preferred. Of *Enterococcus faecalis*, an *Enterococcus faecalis* NF-1011 strain, which is isolated from feces of a healthy individual, is preferred. An *Enterococcus faecalis* NF-1011 strain was deposited in the National Institute of Advanced Industrial Science and Technology, Patent Organism Depositary Center (Central No. 6, 1-1-1 Higashi, Tsukuba, Ibaraki, Japan (postal code 305-8566)), on Oct. 8, 1991, with the accession number FERM P-12564. This strain was then transferred to the international depositary with the accession number FERM BP-10902. In April 2012, the National Institute of Advanced Industrial Science and Technology, Patent Organism Depositary Center was consolidated into the National Institute of Technology and Evaluation (NITE), Patent Microorganisms Depositary, and the microorganism depositary operation has been succeeded by the National Institute of Technology and Evaluation Biotechnology Center, International Patent Organism Depositary (NITE-IPOD) (#120, 2-5-8 Kazusakamatari, Kisarazu-shi, Chiba 292-0818, Japan).

The cells of lactic acid bacteria belonging to the genus *Enterococcus* are not particularly limited as long as they are the entire structure of the lactic acid bacteria belonging to the genus *Enterococcus*. The cells may be viable cells or dead cells. The cells may be a dried product such as a lyophilized product. The viable cells of lactic acid bacteria belonging to the genus *Enterococcus* can be ordered from national or international distribution organizations, such as ATCC, IFO, and JCM, or can be isolated from an organism.

Since viable cells can be easily produced in a large quantity by culture, use of cultured viable cells is economical with low production costs. Viable cells of lactic acid bacteria belonging to the genus *Enterococcus* can be also proliferated by culture according to a known method. For example, a large amount of viable cells can be obtained by seeding the lactic acid bacteria in an appropriate amount of sterile Rogosa liquid medium, statically culturing the bacteria at 35 to 37° C. for 10 to 16 hours in an aerobic manner to obtain a preliminary culture liquid, adding the preliminary culture liquid to a large quantity of sterile Rogosa liquid medium to perform static culture in the same manner. When viable cells are used, a culture liquid itself may be used, or a solid of the culture liquid (e.g., a precipitate obtained by precipitating viable cells in the culture liquid by centrifugation and the like, and optionally washing with a physiological saline solution) can be used, or a suspension of the solid (e.g., a suspension obtained by suspending viable cells in an isotonic solution such as a physiological saline solution) can be used.

The dead cells of lactic acid bacteria belonging to the genus *Enterococcus* are not particularly limited. For example, heat-treated viable cells can be used. The temperature of the heat treatment is not particularly limited as long as it is 100° C. or higher. It is preferably a temperature at which an autoclave treatment can be performed (e.g., 110 to 125° C.). The heat treatment time is, for example, 1 minute or more, preferably 5 to 20 minutes, and more preferably about 5 to 15 minutes.

The cells of a *Lactobacillus Enterococcus faecalis* NF-1011 strain are commercially available, for example, as FK-23 (trademark) from Nichinichi Pharmaceutical Co., Ltd.

In the present invention, the term "cell component of lactic acid bacteria" means a component that is released outside the cells as a result of the destruction of the cell wall of lactic acid bacteria.

The cell component of lactic acid bacteria is not particularly limited. It is, for example, a component in which the cell wall of viable cells is destroyed. The cell wall to be destroyed may be all or part of the cell wall of viable cells. Examples of the cell wall-destroying method include heat treatment, treatment by physical force, treatment with a lytic enzyme, and combinations thereof. Of these, a method comprising treatment with a lytic enzyme is preferred. A method comprising (a) treatment with a lytic enzyme and (b) at least one treatment selected from the group consisting of heat treatment and treatment by physical force (preferably heat treatment) is more preferred; and a method in which (b) at least one treatment selected from the group consisting of heat treatment and treatment by physical force (preferably heat treatment) is performed after (a) treatment with a lytic enzyme is even more preferred.

The temperature of the heat treatment is not particularly limited as long as it is 100° C. or higher. It is preferably a temperature at which autoclave treatment can be performed (e.g., 110 to 125° C.). The heat treatment time is not particularly limited as long as all or part of the cell wall can be destroyed, and can be suitably set according to the temperature of the heat treatment. The heat treatment time is, for example, 1 minute or more, preferably 5 to 20 minutes, and more preferably about 5 to 15 minutes.

The method of treatment by physical force is not particularly limited as long as all or part of the cell wall can be destroyed. Examples include an ultrasonic treatment, French press, and the like.

The enzyme used for the treatment with a lytic enzyme is not particularly limited as long as it can destroy all or part of the cell wall. Various enzymes generally used for lysing bacteria can be used. Examples include lysozyme, actinase, zymolyse, chitarase, mutanosylin, and acromopeptidase. Of these, lysozyme is preferred. One kind of lytic enzyme may be used, and two or more kinds of lytic enzymes may be used in combination.

Conditions for treatment with a lytic enzyme can be suitably determined according to the kind of lytic enzyme, the amount of a lysis target (viable cells), and the like. For example, the lytic enzyme may be added to a viable cell suspension so that the final concentration is 0.01 to 1 mg/mL, and a treatment is performed at 30 to 40° C. for 1 to 10 hours.

The cell component of lactic acid bacteria is not particularly limited as long as it is a component constituting the cells of lactic acid bacteria. The cell component is preferably a water-soluble component. The water-soluble component is obtained, for example, by removing a solid by centrifugation or the like from lactic acid bacteria whose cell wall has been destroyed.

The cell component of *Lactobacillus Enterococcus faecalis* NF-1011 strain is commercially available, for example, as LFK (trademark) from Nichinichi Pharmaceutical Co., Ltd.

Since the external agent of the present invention exhibits effects of hair growth and hair loss prevention due to cells of lactic acid bacteria belonging to the genus *Enterococcus* and cell components thereof, they are suitably used as active ingredients of an external agent for growing hair or preventing hair loss. The external agent of the present invention includes an external drug and a cosmetic. The cosmetic also includes a quasi-drug. The external agent of the present invention is applied to the skin (including the scalp) of mammals, including humans. In the present invention, hair growth includes the concepts of hair development and hair nourishment.

In preparing a drug, the cells of lactic acid bacteria and the cell component thereof are prepared, together with a known ingredient, into the form of an external solid preparation, an external liquid preparation, a spray, an ointment, a cream, a gel, a paste, and the like, thus obtaining an external preparation.

The drug may include one or more kinds of known additives used for an external agent, i.e., one or more kinds of known additives selected from antibacterial agents, coolants, emulsifiers, oils, antioxidants, surfactants, fragrances, UV absorbers, dyes, ethanol, water, moisturizers, thickeners, solubilizers, gelling agents, and the like.

The proportion of cells of lactic acid bacteria or cell component thereof contained in the drug is not particularly limited. The proportion is for example, 0.01 to 99 mass %.

Cosmetics can be formulated in various forms, including an aqueous solution, solubilization, emulsion, oil-liquid, powder, gel, ointment, aerosol, water-oil two-layer form, and water-oil-powder three-layer form.

The cosmetics can also be used for any application. Examples include shampoo, rinse, hair treatment, hair conditioner, hair styling products, hair tonic, hair dye, hair manicure, pomade, hair liquid, hair spray, hair cream, hair growth agents, and the like.

In addition to the cells of lactic acid bacteria or cell component thereof, the cosmetic suitably contains an ingredient that is generally used in cosmetics, as necessary. Examples include a moisturizers, antioxidants, oily components, UV absorbers, surfactants, thickeners, alcohol, colorants, disinfectants, preservatives, fragrances, solvents, pH adjusters, blood circulation stimulants, and the like.

The proportion of the cells of lactic acid bacteria or cell component thereof in the cosmetic is not particularly limited. For example, the proportion is 0.01 to 99 mass %.

Since the cells of lactic acid bacteria belonging to the genus *Enterococcus* and cell components thereof have effects of hair growth and hair loss prevention, they are useful as active ingredients of an external agent for growing hair or preventing hair loss.

EXAMPLES

The following examples are given to illustrate the present invention in more detail. However, the present invention is not limited to these examples.

1. Preparation of Cell Sample: FK-23

An *Enterococcus faecalis* NF-1011 strain was cultured in a liquid medium (glucose: 2%, yeast extract: 2%, peptone: 2%, dipotassium hydrogen phosphate: 4%) at 37° C. for 18 hours. Using a microfiltration membrane, harvesting and washing were performed to collect viable cells. The viable cells were heat-treated at 110° C. for 10 minutes, and then dried by spray drying. The resulting dried dead cells were used as a cell sample (FK-23) in the following experiment.

2. Preparation of Cell Sample: LFK

An *Enterococcus faecalis* NF-1011 strain was inoculated in 10 ml of Rogosa liquid medium and statically cultured (preliminarily cultured) aerobically at 37° C. for 15 hours to obtain a cell solution (seed) having a cell concentration of approximately $10^9$ cells/ml. The cells were inoculated in 10 L of Rogosa liquid medium (cell concentration: $10^6$ cells/ml) and statically cultured aerobically at 37° C. for 16 hours to obtain a cell solution having a viable cell count of approximately $10^9$ cells/ml. The obtained cell solution was harvested by centrifugation (12,000×g for 20 minutes), followed by washing twice with a physiological saline solution (0.85% sodium chloride solution) and suspension in 100 ml of distilled water, thus obtaining a cell suspension. Lysozyme was added to the cell suspension so that the final concentration became 0.1 mg/ml, followed by a treatment at 37° C. for 4 hours. Thereafter, heat treatment at 110° C. for 10 minutes was conducted to obtain treated cells. The resulting treated cells were used as a cell sample (LFK) in the following experiment.

Test Example 1

A hair styling product obtained by suspending 1% of a powder in which FK-23 and LFK were mixed in a ratio of 1:1 in a solution containing ethanol and water as main components was used once a day on a 39-year-old male subject, mainly on the part of the scalp where bare skin was visible and which the subject was concerned with. The time of use was not particularly specified; however, the subject used the product mainly before bedtime and after hair drying when the hair was washed.

FIG. 1 shows photographs representing the crown of the head of a male subject after beginning use. The subject began using the product on Jun. 5, 2018. From June 19 to Jul. 3, 2018, an increase in hair was observed with naked eyes.

Test Example 2

The same styling product as in Test Example 1 was used once a day on five male and female subjects in their 40s to 70s, mainly on the part of the scalp where the bare skin was visible and which the subjects were concerned with. The time of use was not particularly specified; however, the subject used the product mainly before bedtime and after hair drying when the hair was washed.

Figure 2:
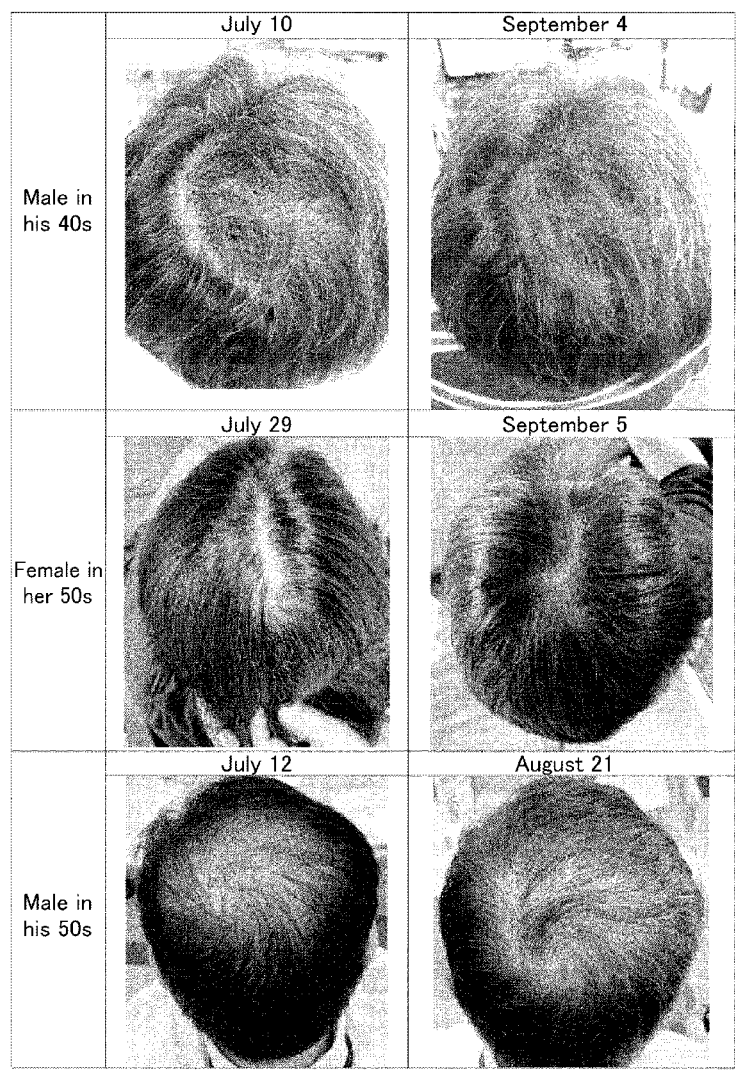
FIG. 2 shows photographs representing the crown of the head of each subject in Test Example 2.
Figure 3:
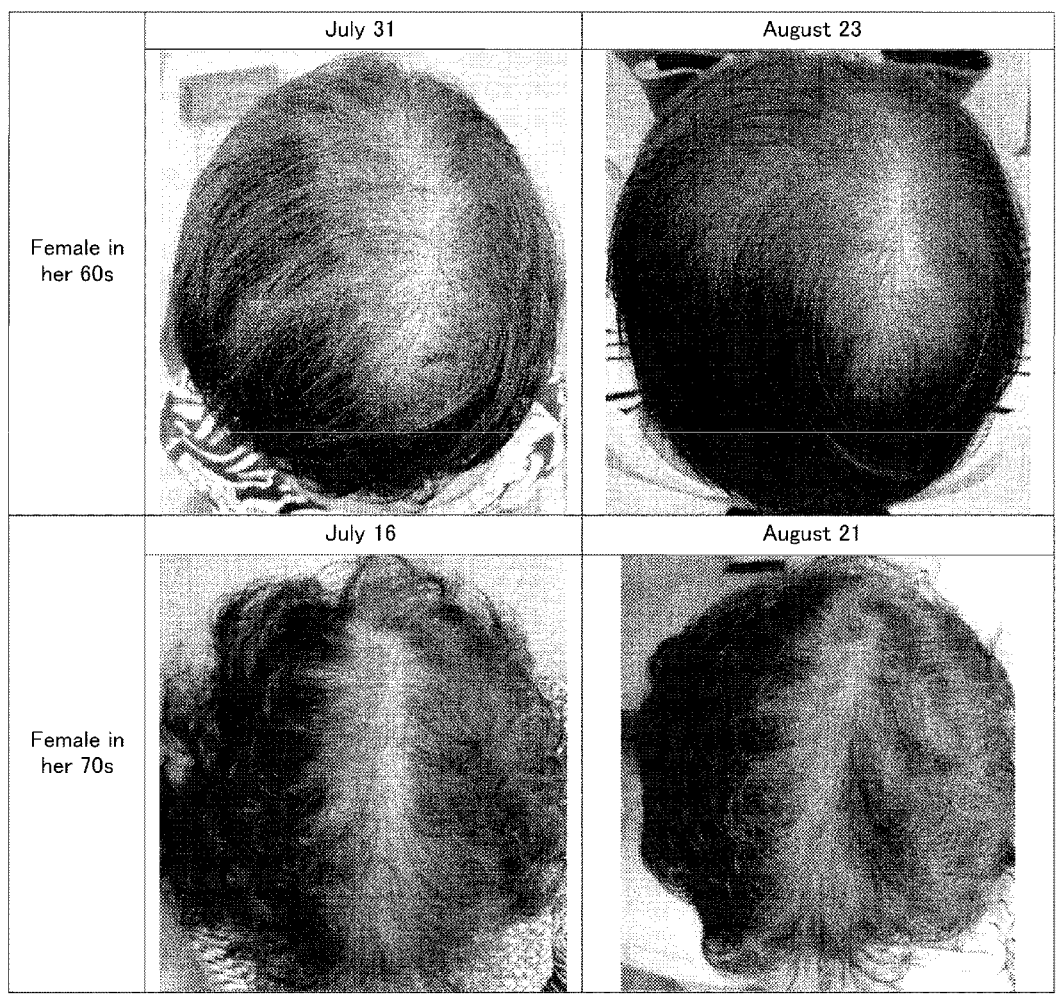
FIG. 3 shows photographs representing the crown of the head of each subject in Test Example 2.

FIGS. 2 and 3 show photographs representing the crown of the head of each subject after beginning use. It was confirmed that in the subjects who quickly achieved results, the bare skin became less noticeable by the fourth week of use, and in the subjects who slowly achieved results, the bare skin became less noticeable by the eighth week.

The invention claimed is:
1. A method for growing hair or preventing hair loss, comprising the step of applying at least one member selected from the group consisting of cells of lactic acid bacteria belonging to the genus *Enterococcus* and cell components thereof to the skin of a mammal in need of growing hair or preventing hair loss, wherein the lactic acid bacteria belonging to the genus *Enterococcus* are *Enterococcus faecalis*.

2. The method according to claim 1, wherein the lactic acid bacteria belonging to the genus *Enterococcus* are *Enterococcus faecalis* NF-1011 strain (FERM BP-10902).

3. The method according to claim 1, wherein the cells are dead cells.

4. The method according to claim 1, wherein the cell component of lactic acid bacteria is a component obtained by subjecting the lactic acid bacteria to a lytic enzyme treatment and a heat treatment, the lytic enzyme is at least one selected from the group consisting of lysozyme, actinase, zymolyse, chitarase, mutanosylin, and acromopeptidase, and the temperature of the heat treatment is 100° C. or higher.

* * * * *